(12) United States Patent
Mortimore et al.

(10) Patent No.: US 7,737,151 B2
(45) Date of Patent: Jun. 15, 2010

(54) PYRAZINE KINASE INHIBITORS

(75) Inventors: Michael Mortimore, Burford (GB); Julian M. C. Golec, Faringdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 456 days.

(21) Appl. No.: 11/505,637

(22) Filed: Aug. 17, 2006

(65) Prior Publication Data

US 2007/0173516 A1  Jul. 26, 2007

Related U.S. Application Data

(60) Provisional application No. 60/709,541, filed on Aug. 18, 2005, provisional application No. 60/709,760, filed on Aug. 19, 2005, provisional application No. 60/720,596, filed on Sep. 26, 2005.

(51) Int. Cl.
  *A61K 31/4965* (2006.01)
(52) U.S. Cl. .................. 514/255.06; 544/408; 548/190; 548/371.4
(58) Field of Classification Search .................. 544/408
  See application file for complete search history.

(56) References Cited

U.S. PATENT DOCUMENTS

| | | | |
|---|---|---|---|
| 3,133,081 A | 5/1964 | Lafferty et al. |
| 3,755,322 A | 8/1973 | Winter et al. |
| 3,935,183 A | 1/1976 | Baron et al. |
| 3,998,951 A | 12/1976 | Harmish et al. |
| 4,051,252 A | 9/1977 | Mayer et al. |
| 4,493,726 A | 1/1985 | Burdeska et al. |
| 4,540,698 A | 9/1985 | Ishikawa et al. |
| 4,711,951 A | 12/1987 | Axen et al. |
| 5,124,441 A | 6/1992 | Carlsson et al. |
| 5,710,158 A | 1/1998 | Myers et al. |
| 5,916,908 A | 6/1999 | Giese et al. |
| 5,972,946 A | 10/1999 | Murata et al. |
| 6,093,716 A | 7/2000 | Davis et al. |
| 6,184,226 B1 | 2/2001 | Chakravarty et al. |
| 6,200,977 B1 | 3/2001 | Cushing et al. |
| 6,277,989 B1 | 8/2001 | Chakravarty et al. |
| 6,495,582 B1 | 12/2002 | Hale et al. |
| 6,528,509 B1 | 3/2003 | Hale et al. |
| 6,528,513 B2 | 3/2003 | Cushing et al. |
| 6,558,657 B1 | 5/2003 | Mandeville, III et al. |
| 6,562,971 B2 | 5/2003 | Frauenkron et al. |
| 6,579,983 B1 | 6/2003 | Batchelor et al. |
| 6,589,958 B1 | 7/2003 | Frietze |
| 6,593,326 B1 | 7/2003 | Bradbury et al. |
| 6,610,677 B2 | 8/2003 | Davies et al. |
| 6,613,776 B2 | 9/2003 | Knegtel et al. |
| 6,638,926 B2 | 10/2003 | Davies et al. |
| 6,642,227 B2 | 11/2003 | Cao et al. |
| 6,653,300 B2 | 11/2003 | Bebbington et al. |
| 6,653,301 B2 | 11/2003 | Bebbington et al. |
| 6,656,939 B2 | 12/2003 | Bebbington et al. |
| 6,660,731 B2 | 12/2003 | Bebbington et al. |
| 6,664,247 B2 | 12/2003 | Bebbington et al. |
| 6,696,452 B2 | 2/2004 | Davies et al. |
| 6,727,251 B2 | 4/2004 | Bebbington et al. |
| 6,743,791 B2 | 6/2004 | Cao et al. |
| 6,838,464 B2 | 1/2005 | Pease et al. |
| 6,841,579 B1 | 1/2005 | Plowman et al. |
| 6,846,928 B2 | 1/2005 | Bebbington et al. |
| 6,949,544 B2 | 9/2005 | Bethiel et al. |
| 6,989,385 B2 | 1/2006 | Bebbington et al. |
| 7,008,948 B2 | 3/2006 | Bebbington et al. |
| 7,084,159 B2 | 8/2006 | Cao et al. |
| 7,087,603 B2 | 8/2006 | Bebbington et al. |
| 7,091,343 B2 | 8/2006 | Bebbington et al. |
| 7,098,330 B2 | 8/2006 | Bebbington |
| 7,115,739 B2 | 10/2006 | Bebbington et al. |
| 7,179,826 B2 | 2/2007 | Bebbington et al. |
| 7,253,187 B2 | 8/2007 | Cao et al. |
| 2001/0018436 A1 | 8/2001 | Cushing et al. |
| 2002/0052386 A1 | 5/2002 | Armistead et al. |
| 2002/0065270 A1 | 5/2002 | Moriarty et al. |
| 2003/0004161 A1 | 1/2003 | Bebbington et al. |

(Continued)

FOREIGN PATENT DOCUMENTS

DE  2458965  6/1976

(Continued)

OTHER PUBLICATIONS

Ife, R.J. et al., "Reversible Inhibitors of the Gastric (H+/K+)-ATPase. 5. Substituted 2,4-Diaminoquinazolines and Thienopyrimidines", J. Med. Chem., 38(14); 2763-2773 (1995).

(Continued)

*Primary Examiner*—James O Wilson
*Assistant Examiner*—Brian McDowell
(74) *Attorney, Agent, or Firm*—H. Joon Chung

(57) ABSTRACT

The present invention relates to compounds useful as inhibitors of protein kinases of the following formula:

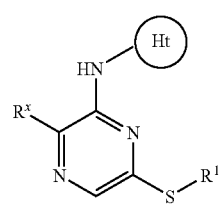

or a pharmaceutically acceptable salt thereof. The invention also provides pharmaceutically acceptable compositions comprising those compounds and methods of using the compounds and compositions in the treatment of various disease, conditions, and disorders. The invention also provides processes for preparing compounds of the inventions.

11 Claims, No Drawings

U.S. PATENT DOCUMENTS

| | | |
|---|---|---|
| 2003/0004164 A1 | 1/2003 | Bebbington et al. |
| 2003/0022885 A1 | 1/2003 | Bebbington et al. |
| 2003/0036543 A1 | 2/2003 | Bebbington et al. |
| 2003/0055044 A1 | 3/2003 | Davies et al. |
| 2003/0055068 A1 | 3/2003 | Bebbington et al. |
| 2003/0064981 A1 | 4/2003 | Knegtel et al. |
| 2003/0064982 A1 | 4/2003 | Davies et al. |
| 2003/0069239 A1 | 4/2003 | Cai et al. |
| 2003/0069248 A1 | 4/2003 | Chakravarty et al. |
| 2003/0073687 A1 | 4/2003 | Bebbington et al. |
| 2003/0078275 A1 | 4/2003 | Bebbington et al. |
| 2003/0083327 A1 | 5/2003 | Davies et al. |
| 2003/0087922 A1 | 5/2003 | Bethiel et al. |
| 2003/0092714 A1 | 5/2003 | Cao et al. |
| 2003/0096813 A1 | 5/2003 | Cao et al. |
| 2003/0096816 A1 | 5/2003 | Cao et al. |
| 2003/0105090 A1 | 6/2003 | Bebbington et al. |
| 2003/0144309 A1 | 7/2003 | Choon-Moon |
| 2003/0171389 A1 | 9/2003 | Bemis et al. |
| 2003/0187002 A1 | 10/2003 | Mortlock et al. |
| 2003/0199526 A1 | 10/2003 | Choquette et al. |
| 2003/0207873 A1 | 11/2003 | Harrington |
| 2003/0225073 A1 | 12/2003 | Bebbington et al. |
| 2004/0002496 A1 | 1/2004 | Bebbington et al. |
| 2004/0009974 A1 | 1/2004 | Bebbington et al. |
| 2004/0009996 A1 | 1/2004 | Moon et al. |
| 2004/0023963 A1 | 2/2004 | Cao et al. |
| 2004/0029857 A1 | 2/2004 | Hale et al. |
| 2004/0097501 A1 | 5/2004 | Bebbington et al. |
| 2004/0097531 A1 | 5/2004 | Ledeboer et al. |
| 2004/0157893 A1 | 8/2004 | Bebbington et al. |
| 2004/0214814 A1 | 10/2004 | Bebbington et al. |
| 2004/0229875 A1 | 11/2004 | Cao et al. |
| 2005/0004110 A1 | 1/2005 | Bebbington et al. |
| 2005/0038023 A1 | 2/2005 | Bebbington et al. |
| 2005/0234059 A1 | 10/2005 | Hale et al. |
| 2006/0270660 A1 | 11/2006 | Charrier et al. |

FOREIGN PATENT DOCUMENTS

| | | |
|---|---|---|
| EP | 0019811 | 12/1980 |
| EP | 136976 | 4/1985 |
| EP | 0302312 | 2/1989 |
| GB | 2052487 | 1/1981 |
| JP | 10130150 | 5/1998 |
| JP | 2000026421 | 1/2000 |
| JP | 0665237 | 10/2007 |
| WO | 9208715 | 5/1992 |
| WO | 9322681 | 11/1993 |
| WO | 9509851 | 4/1995 |
| WO | 9515758 | 6/1995 |
| WO | 9614843 | 5/1996 |
| WO | 9709325 | 3/1997 |
| WO | 9719065 | 5/1997 |
| WO | 9802434 | 1/1998 |
| WO | 9811095 | 3/1998 |
| WO | 9814450 | 4/1998 |
| WO | 9816502 | 4/1998 |
| WO | 9838171 | 9/1998 |
| WO | 9918781 | 4/1999 |
| WO | 9941253 | 8/1999 |
| WO | 9947154 | 9/1999 |
| WO | 9962518 | 12/1999 |
| WO | 9965897 | 12/1999 |
| WO | 0012497 | 3/2000 |
| WO | 0021955 | 4/2000 |
| WO | 0038675 | 7/2000 |
| WO | 0039101 | 7/2000 |
| WO | 0042029 | 7/2000 |
| WO | 0059509 | 10/2000 |
| WO | 0078757 | 12/2000 |
| WO | 0112621 | 2/2001 |
| WO | 0125220 | 4/2001 |
| WO | 0139777 | 6/2001 |
| WO | 0140215 | 6/2001 |
| WO | 0144242 | 6/2001 |
| WO | 0147879 | 7/2001 |
| WO | 0160816 | 8/2001 |
| WO | 0164655 | 9/2001 |
| WO | 0174768 | 10/2001 |
| WO | 0179198 | 10/2001 |
| WO | 0208244 | 1/2002 |
| WO | 0218346 | 3/2002 |
| WO | 0222601 | 3/2002 |
| WO | 0224667 | 3/2002 |
| WO | 0247690 | 6/2002 |
| WO | 0250065 | 6/2002 |
| WO | 0250066 | 6/2002 |
| WO | 02059111 A2 | 8/2002 |
| WO | 02059112 A2 | 8/2002 |
| WO | 02066461 A1 | 8/2002 |
| WO | 0279197 | 10/2002 |
| WO | 04000833 | 12/2003 |
| WO | 2004013140 | 2/2004 |

OTHER PUBLICATIONS

Tanzi, K. et al., "Purines. X. Reactivities of Methyl Groups on 9-Phenylpurines : Condensation with an Aldehyde or an Ester, and Oxidation with Selenium Dioxide", Chem. Phar. Bull., 40 (1), 227-229 (1992).

Charpiot, B. et al., "Quinazolines: Combined type 3 and 4 phosphodiesterase inhibitors", Bioorg. Med. Chem. Lett., 8 (20), 2891-2896 (1998).

Shikhaliev, K.S. et al., "Heterocyclization of quinazol-2-ylguanidines. 1. Reaction with amino acids", Chem. Heterocycl. Compd., 35 (7), 818-820 (1999).

Singh, S.P. et al., "Synthesis & Mass Spectra of Some Substituted 2-(2'-Benzazolylamino)pyrimidines", Indian J. Chem. Sect. B, 22(1); 37-42 (1983).

Ti, J. et al., "Anticandidal activity of pyrimidine-peptide conjugates", J. Med. Chem., 23(8), 913-918 (1980).

Kretzschmar, E. et al., "Synthese von 2,6-disubstituierten 4-Hydroxy-5,6,7,8-tetrahydropyrido[4,3-d]pyrimidinen", Pharmazie, 43(7), 475-476 (1988).

Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., 43(22), 4288-4312 (2000).

Nugent, R.A. et al., "Pyrimidine Thioethers: A Novel Class of HIV-1 Reverse Transcriptase Inhibitors with Activity Against BHAP-Resistant HIV", J. Med. Chem., 41, 3793-3803 (1998).

Myers, M.R. et al., "The synthesis and SAR of new 4-(N-alkyl-N-phenyl)amino-6,7-dimethoxyquinazolines and 4-(N-alkyl-N-phenyl)aminopyrazolo[3,4-d]pyrimidines, inhibitors of CSF-1R tyrosine kinase activity", Bioorg. Med. Chem. Lett., 7, 4, 421-424 (1997).

Agarwal, N. et al., "Suitably functionalised pyrimidines as potential antimycotic agents", Bioorg. Med. Chem. Lett., 10, 8, 703-706 (2000).

Crespo, M.I. et al., "Design, Synthesis, and Biological Activities of New Thieno[3,2-d]pyrimidines as Selective Type 4 Phosphodiesterase Inhibitors", J. Med. Chem., 41 (21), 4021-4035 (1998).

Noell, C.W. et al., "Potential Purine Antagonists. XX. The Preparation and Reactions of Some Methylthiopurines", J. Am. Chem. Soc., 81(22), 5997-6007 (1959).

Lubbers, T. et al., "Design, synthesis, and structure-activity relationship studies of ATP analogues as DNA gyrase inhibitors", Bioorg. Med. Chem. Lett., 10, 8, 821-826 (2000).

D'Atri, G. et al., "Novel pyrimidine and 1,3,5-triazine hypolipemic agents", J. Med. Chem. 27(12), 1621-1629 (1984).

Venugopalan, B. et al., "Synthesis and antimalarial activity of pyrido[3,2-f]quinozalines and their oxides", Indian J. Chem. Sect. B, 34, 9, 778-790 (1995).

Curd, F.H.S. et al, "Synthetic antimalarials. Part XVII. Some aminoalkylaminoquinoline derivatives", J. Chem. Soc., 899-909 (1947).

Haworth, R.D. et al., "Synthetic antimalarials. Part XXVII. Some derivatives of phthalazine, quinoxaline, and isoquinoline", J. Chem. Soc., 777-782 (1948).

Nair, M.D., et al., "3-Chloroisocarbostyril & Its Chlorination Products", Indian J. Chem., 467-470 (1967).

Jeffery, J.E. et al., "Synthesis of sibutramine, a novel cyclobutylalkylamine useful in the treatment of obesity, and its major human metabolites", J. Chem. Soc., Perkin Trans. 1, 21, 2583-2589 (1996).

Gnecco, D. et al., "An Improved Preparation of 1-Methyl-4-Cyano-4-phenylpiperidine", Org. Prep. Proced. Int., 18 (4), 478-480 (1996).

Fedorynski, M. et al., "Synthesis of 1-Arycyclopropanecarbonitriles under Phase-transfer Catalytic Conditions", Org. Prep. Proced. Int., 27(3), 355-359 (1995).

Suzuki, S. et al., "Application of electrogenerated triphenylmethyl anion as a base for alkylation of arylacetic esters and arylacetonitriles and isomerization of allylbenzenes", Can. J. Chem., 72(2): 357-361 (1994).

Prasad, G. et al., "18-Crown-6 as a catalyst in the dialkylation of o-nitrophenacyl derivatives", J. Org. Chem., 25, 7188-7190 (1991).

Moss, R.A. et al., "Conversion of 'Obstinate' Nitriles to Amidines by Garigipati's Reaction", Tetrahedron Lett., 36(48), 8761-8764 (1995).

Garigipati, R.S., "An efficient conversion of nitriles to amidines", Tetrahedron Lett., 31(14), 1969-1972 (1990).

Warner, S.L. et al, "Targeting Aurora-2 Kinase in Cancer," Mol. Cancer Thera., 2, 589-585, 2003.

Wagman, A.S. et all, "Discovery and Development of GSK3 Inhibitors for the Treatment of Type 2 Diabetes," Current Pharmaceutical Design, 10, 1105-1137 (2004).

Nezu, Y. et al., "Dimethoxypyrimidines as Novel Herbicides. Part 2. Synthesis and Herbicidal Activity of Dimethoxyphenoxyphenoxypyrimidines and Analogues," Pestic. Sci., 47: 115-124 (1996).

Tanaka, T.U. et al., "Evidence that the Ipl1-Sli15 (Aurora Kinase-INCENP) Complex Promotes Chromosome Bi-orientation by Altering Kinetochore-Spindle Pole Connections," Cell, 108, 317-329 (2002).

Soriano, P. et al., "Targeted Disruption of the C-SIC Pmto-Oncogene Leads to Osteopetrosis in Mice," Cell, 64: 693-702, (1991).

Campbell, S.F. et al., "2,4-Diamino-6,7-dimethoxyquinazolines. 3.2-(4-Heterocyclylpiperazin-l-yl) Derivatives as α1-Adrenoceptor Antagonists and Antihypertensive Agents," J. Med. Chem., 30, 1794-1798 (1987).

Casanova, B. et al., "Revisión crítica de la patogenia actual de la esclerosis múltiple y futuras direcciones posibles," Rev. Neurol., 28 (9): 909-915 (1999).

Cline, G.W. et al., "Effects of a Novel Glycogen Synthase Kinase-3 Inhibitor on Insulin-Stimulated Glucose Metabolism in Zucker Diabetic Fatty (fa/fa) Rats," Diabetes, 51, 2903-2910 (2002).

Simone, J.V., "Oncology: Introduction" in Cecil Textbook in Medicine, 20th ed., vol. 1, 1004-1010 (1996).

Coleman, R.A., "The Biological Evaluation of New Compounds" in Medicinal Chemistry: Principles and Practice, King, Frank D. ed, Royal Society of Chemistry, 53-66 (1994).

The Condensed Chemical Dictionary, Sixth Edition by Arthur and Elizabeth Rose, 38 (1961).

Damasio, A.R., "Alzheimer's Disease and Related Dementia," in Cecil Textbook of Medicine, 20th ed., 2: 1992-1996.

Rogers, E. et al., "The aurora kinase AIR-2 functions in the release of chromosome cohesion in *Caenorhabditis elegans* meiosis," J. Cell Biol., 157(2): 219-229 (2002).

Fisher A., "Therapeutic Strategies in Alzheimer's Disease: M1 Muscarinic Agonists," Jpn. J. Pharmacol., 84(2):101-12 (2000).

Frame, M.C., "Src in cancer: deregulation and consequences for cell behaviour," Biochimica et Biophysica Acta., 1602, 114-130 (2002).

Frampton, J.E. et al., "Pentoxifylline (Oxpentifylline)—A Review of its Therapeutic Efficacy in the Management of Peripheral Vascular and Cerebrovascular Disorder," Drugs & Aging, 7(6): 480-503 (1995).

Ganellin, C.R., "Past Approaches to Discovering New Drugs as Medicines" in Medicinal Chemistry, Principles and Practices, King, Frank D. ed, Royal Society of Chemistry, 189-205 (1994).

Hamdane, M. et al., "A Therapeutic Target in Alzheimer Neurodegeneration," J. Mol. Neurosci., 19(3): 275-87 (2002).

Hardt, S.E. et al., "Glycogen Synthase Kinase-3β—A Novel Regulator of Cardiac Hypertrophy and Development," Circulation Research, 90: 1055-1063 (2002).

Parnell, E.W., "2-Cyano-4-nitrophenylhydrazine and 3-Amino-5-nitroindazole", J. Chem. Soc., 2363-2365 (1959).

Heaney, F. et al., "Pyrimidine annelated heterocycles—synthesis and cycloaddition of the first pyrimido[1,4]diazepine N-oxides," J. Chem. Soc., Perkin Trans. 1, 622-632 (2001).

Hendriksen, E.J. et al., "Modulation of muscle insulin resistance by selective inhibition of GSK-3 in Zucker diabetic fatty rats," Am. J. Physiol. Endocrinol. Metab., 284: E892-E900 (2003).

Okafor, C.O., "Studies in the Heterocyclic Series. X. 1,3,9-Triazaphenothiazine Ring System, a New Phenothiazine Ring," J. Org. Chem., 40(19): 2753-2755 (1975).

100. Jambhekar, S.S., "Biopharmaceutical Properties of Drug Substances" in Principles of Medicinal Chemistry, 4th ed., 12-24, (1995).

Alonso, M. et al., "GSK-3 Inhibitors: Discoveries and Developments", Current Medicinal Chemistry, 11, 755-763 (2004).

Anonymous, "Vertex Inhbitors of Aurora-2, glycogen synthase kinase-3 and Src Kinase", Expert Opin. Ther. Patents, 14(3): 439-443 (2004).

Baig, G.U. et al., "Triazines and Related Products. Part 28' Conversion of 3-Aryl-I-(2-cyanopheny1) triazenes into 3-Arylqu i nazol i n-4(3H) -ones with Formamide" J. Chem. Soc. Perkin Trans. I, 3765-2766 (1984).

Bischoff, J.R., et al., "A homologue of *Drosophila aurora* kinase is oncogenic and amplified in human colorectal cancers", The EMBO Journal, 17(11): 3052-3065 (1998).

Bischoff, J.R., et al., "The Aurora/lpl1p kinase family: regulators of chromosome segregation and cytokinesis", Cell Biology, 9, 454-459 (1999).

Brunswick, D.J. et al., "Cyclic Amidines. Part XXII. Novel Isomerism of Disubstituted Tricycioquinazolines and Molecular Orientations in Carcinogenesis", J. Chem. Soc. (C), 2641-2647 (1970).

Wolff, M.E., "Burger's Medicinal Chemistry and Drug Discovery," 5th ed., vol. 1: Principles and Practice, 975-977 (1995).

Cohen, P. et al., "The renaissance of GSK3," Nat. Rev. Mol. Biol., 2, 769-776 (2001).

Eldar-Finkelman, H. et al., "Challenges and opportunities with glycogen synthase kinase-3 inhibitors for insulin resistance and Type 2 diabetes treatment," Expert Opinion on Investigational Drugs, 12(9): 1511-1519 (2003).

Layzer, R.B., "Section Five—Degenerative Diseases of the Nervous System" in Cecil Textbook of Medicine, 20th ed., 2: 2050-2057 (1996).

Lee, S.J. et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities," J. Med. Chem., 38 (18): 3547-3557 (1995).

Medwid, J.B. et al., "Preparation of Triazolo[ 1,5-c]pyrimidines as Potential Antiasthma Agents," J. Med. Chem. 33, 1230-1241 (1990).

Nezu, Y. et al., "Dimethoxypyrimidines as Novel Herbicides. Part 1. Synthesis and Herbicidal Activity of Dimethoxyphenoxyphenoxypyrimidines and Analogues," Pestic. Sci., 47: 103-113 (1996).

Cohen, P., "Dissection of the Protein Phosphorylation Cascades Involved in Insulin and Growth Factor Action", Biochem. Soc. Trans., 21, 555-567 (1993).

Haq, S. et al., "Glycogen Synthase Kinase-3β Is a Negative Regulator of Cardiomyocyte Hypertrophy", J. Cell Biol., 151(1), 117-129 (2000).

Fischer, P.M. et al., "Inhibitors of Cyclin-Dependent Kinases as Anti-Cancer Therapeutics", Current Med. Chem., 7, 1213-1245 (2000).

Mani, S. et al., "Cyclin-dependent kinase: novel anticancer agents", Exp. Opin. Invest. Drugs., 8, 1849-1870 (2000).
Fry, D.W. et al., "Inhibitors of cyclin-dependent kinases as therapeutic agents for the treatment of cancer", Current Opin. Oncol. Endoc. & Metab. Investig., 2-40-59 (2000).
Bokemeyer, D. et al., "Multiple intracellular MAP kinase signaling cascades", Kidney Int., 49, 1187-1198 (1996).
Anderson, N.G. et al., "Multiple intracellular MAP kinase signaling cascades", Nature, 343, 651-653 (1990).
Crews, C.M. et al., "The Primary Structure of MEK, a Protein Kinase That Phosphorylates the ERK Gene Product", Science, 258, 478-480 (1992).
Bjorbaek, C. et al, "Divergent Functional Roles for p90rsk Kinase Domains", J. Biol. Chem., 270(32), 18848-18552 (1995).
Rouse, J. et al., A Novel Kinase Cascade Triggered by Stress and Heat Shock That Stimulates MAPKAP Kinase-2 and Phosphorylation of the Small Heat Shock Proteins, Cell, 78, 1027-1037 (1994).
Raingeaud, J. et al., MMK3- and MMK6-Regulated Gene Expression Is Mediated by p38 Mitogen-Activated Protein Kinase Signal Transduction Pathway, Mol. Cell. Biol., 16, 1247-1255 (1996).
Chen, R.H. et al., "Phosphorylation of the c-Fos transrepression domain by mitogen-activated protein kinase and 90-kDa ribosomal S6 kinase", Proc. Natl. Acad. Sci. USA, 90, 10952-10956 (1993).
Moodie, S.A. et al., "Complexes of Ras-GTP with Raf-1 and Mitogen-Activated Protein Kinase Kinase", Science, 260 (5114), 1658-1661 (1993).
Frey, R.S. et al., "Involvement of Extracellular Signal-regulated Kinase 2 and Stress-activated Protein Kinase/Jun N-Terminal Kinase Activation by Transforming Growth Factor β in the Negative Growth Control of Breast Cancer Cells", Cancer Res., 57, 628-633 (1997).
Sivaraman, V.S., et al., "Hyperexpression of Mitogen-activated Protein Kinase in Human Breast Cancer", J. Clin. Invest., 99(7), 1478-1483 (1997).
Whelchel, A. et al., "Inhibition of ERK Activation Attenuates Endothelin-stimulated Airway Smooth Muscle Cell Proliferation", Am. J. Respir. Cell Mol. Biol., 16, 589-596 (1997).
Yuan, Z.Q. et al., "Frequent activation of AKT2 and induction of apoptosis by inhibition of phosphoinositide-3-OH kinase/Akt pathway in human ovarian cancer", Oncogene, 19, 2324-2330 (2000).
Kazuhiko, N. et al., "Akt/Protein Kinase B Prevents Injury-Induced Motoneuron Death and Accelerates Axonal Regeneration", J. of Neuroscience, 20(8), 2875-2986 (2000).
Molina, T.J. et al., "Profound block in thymocyte development in mice lacking p56lck", Nature, 357, 161-164 (1992).
Kimura, M. et al., "Cell Cycle-dependent Expression and Centrosome Localization of a Third Human Aurora/Ipl1-related Protein Kinase, AIK3", J. Biol. Chem., 274(11), 13766-13771 (1997).
Harrington, E.A. et al., "VX-680, a potent and selective small-molecule inhibitor of the Aurora kinases, suppresses tumor growth in vivo," Nat. Med., 10(3): 262-267 (2004).
Heutink, P., "Untangling tau-related dementia", Hum. Mol. Genet., 9(6): 979-986 (2000).
Nigg, E.A., "Mitotic Kinases as Regulators of Cell Division and its Checkpoints," Nat. Rev. Mol. Cell Biol., 2: 21-32 (2001).
Traxler, P. et al., "Use of a Pharmacophore Model for the Design of EGF-R Tyrosine Kinase Inhibitors: 4-(Phenylamino)pyrazolo[3,4-d]pyrimidines," J. Med. Chem., 40, 3601-3616 (1997).
CAPLUS listing Accession No. 1994:292136, Nakajima, Y. et al., "Pyrazoles agricultural and horticultural bactericides," JP 06065237 (1994).
Database CA "Online!" Chemical Abstract Service, Columbus, OH, US; Kelarev, V.I. et al., "Synthesis of amino derivatives of 1,3,5-triazine containing 1,3-4-thiadiazole fragments," Database Accession No. 1998:69514 XP002242653 abstract & Izvestiya Vysshikh Uchebnkh Zavedenii, Khimiya I Khimicheskaya Tekhnologiya, 40(5): 27-32 (1997).
Chalmers, D.T. et al., "Corticotrophin-releasing factor receptors: from molecular biology to drug design," TiPS, 17, 769-776 (2001).
Kim, L. et al., "GSK3, a master switch regulating cell-fate specification and tumorigenesis," Current Opinion in Genetics & Development, 10:508-514 (2000).
Lyrer, P., Schweiz. Med. Woohen Schr., 124(45); 2005-2012 (1994).

Banker, G.S. et al., "Modern Pharmaceutics", 451 & 596, 3rd ed., Marcel Dekker, New York (1996).
Lovestone, S. et al., "Alzheimer's disease-like phosphorylation of the microtubule-associated protein tau by glycogen synthase kinase-3 in transfected mammalian cells", Curr. Biol., 4(12), 1077-86 (1994).
Ivashchenko A. V. et al., "Synethsis and Study of Heteroaromatic Ligands Containing a Pyrimidine Ring", Khim. Geterotsikl. Soedin., (12), 1673-7, (1980) (in English).
Brownlees, J. et al., "Tau phosphorylation in transgenic mice expressing glycogen synthase kinase-3beta transgenes", Neuroreport., 8(15), 3251-5 (1997).
Biagi, G. et al., "Synthesis of 4,6 Disubstituted and 4,5,6-Trisubstituted-2-Phenyl-pyrimidines and Their Affinity Towards A1 Adenosine Receptors", Farmaco., 52(1), 61-65 (1997).
Ali, N.M. et al, "Palladium-Catalyzed Cross Coupling Reactions of Arylboronic Acids with Pi-Deficient Heteroaryl Chlorides" Tetrahedron, 48 (37), 8117-8126 (1992).
Zhang, Z. et al., "Destabilization of β catenin by mutations in presenilin-1 potentiates neuronal apoptosis", Nature, 395, 698-702 (1998).
Takashima, K. et al., "Tau Protein Kinase I is Essential for Amyloid β-Protein-Induced Neurotoxicity", PNAS 90, 7789-7793 (1993).
Pei, J. et al., "Distribution, Levels, and Activity of Glycogen Synthase Kinase-3 in the Alzheimer Disease Brain", J. Neuropathol. Exp., 56, 70-78 (1997).
IUPAC Compendium of Chemical Terminology on a definition of "aliphatic compounds" found from http://www.chemsoc.org/chembytes/goldbook/index.htm (last visited on Nov. 18, 2007).
Glossary of Class Names of Organic Compounds and Reactive Intermediates Based on Structure found from http://www.chem.qmul.ac.uk/iupac/class/index.html (last visited on Nov. 18, 2007).
Nomenclature found from http://www.cem.msu.edu/~reusch/VirtualText/nomen1.htm (last visited on Nov. 18, 2007).
Coghlan, M.P. et al., "Selective small molecule inhibitors of glycogen synthase kinase-3 modulate glycogen metabolism and gene transcription", Chemistry & Biology, 7, 793-83 (2000).
Klein, P.S. et al., "A molecular mechanism for the effect of lithium on development", PNAS, 93: 8455-8459 (1996).
Cross, D.A.E. et al., "The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf", Biochem J., 303: 21-26 (1994).
Massillon, D. et al., "Identification of the glycogenic compound 5-iodotubercidin as a general protein kinase inhibitor", Biochem J., 299: 123-128 (1994).
Fox T. et al., "A single amino acid substitution makes ERK2 susceptible to pyridinyl imidazole inhibitors of p38 MAP kinase", Protein Sci., 7: 2249-2255 (1998).
Takayanagi, H. et al., "Suppression of arthritic bone destruction by adenovirus-mediated csk gene transfer to synoviocytes and osteoclasts", J. Clin. Invest., 104, 137-146 (1999).
Boschelli et al., "Small molecule inhibitors of Src family kinases", Drugs of the Future, 25(7): 717-736 (2000).
Talamonti, M.S. et al., "Increase in activity and level of pp60c-src in progressive stages of human colorectal cancer", J Clin Invest., 91(1): 53-60 (1993).
Lutz, M.L. et al., "Overexpression and Activation of the Tyrosine Kinase Src in Human Pancreatic Carcimona", Biochem. Biophys. Res. 243, 503-508 (1998).
Rosen, N. et al., "Analysis of pp60c-src Protein Kinase Activity in Human Tumor Cell Lines and Tissues", J.Biol. Chem., 261, 13754-13759 (1986).
Bolen, J.B. et al., "Activation of pp60c-src protein kinase activity in human colon carcinoma", PNAS, 84, 2251-2255 (1987).
Masaki, T. et al., "pp60c-src Activation in Hepatocellular Carcinoma of Humans and LEC Rats", Hapatology, 27, 1257 (1998).
Biscardi, J.S. et al., "c-Src, Receptor Tyrosine Kinases, and Human Cancer", Adv. Cancer Res., 76, 61 (1999).
Lynch, S.A. et al., "Increased Expression of the src Proto-Oncogene in Hairy Cell Leukemia and a Subgroup of B-Cell Lymphomas", Leukemia, 7(9), 1416-1422 (1993).

Wiener, J.R., "Decreased Src Tyrosine Kinase Activity Inhibits Malignant Human Ovarian Cancer Tumor Growth in a Nude Mouse Model", Clin. Cancer Res., 5, 2164-2170 (1999).

Staley, C.A. et al., "Decreased Tumorigenicity of a Human Colon Adenocarcinoma Cell Line by an Antisense Expression Vector Specific for c-Src", Cell Growth Diff., 8, 269-274 (1997).

Singhal, N. et al., "Synthesis and Antimalarial Activity of Some New Quinazoline Derivatives", Indian Chem. Soc., 61, 690-693 (1984).

Kim, Y.Z. et al., "Synthesis and Antimicrobial Activity of Novel [(3-Aminopyrimidiniumyl)thio]methyl Cephalosporins", J. Med. Chem., 37(22); 3828-3833 (1994).

Rueeger, H et al., "Design, synthesis and SAR of a series of 2-substituted 4-amino-quinazoline neuropeptide Y Y5 receptor antagonists", Bioorg. Med. Chem. Lett., 10(11), 1175-1180 (2000).

Gershon, H. et al., "Pyrimidines. 7. A Study of the Chlorination of Pyrimidines with Phosphorus Oxychloride in the Presence of N,N-Dimethylaniline", J. Heterocyclic Chem., 21, 1161-1167 (1984).

PYRAZINE KINASE INHIBITORS

CROSS REFERENCE TO RELATED APPLICATIONS

This present application claims the benefit, under 35 U.S.C. §119, to U.S. Provisional Application Nos. 60/709,541 filed Aug. 18, 2005; 60/709,760 filed Aug. 19, 2005; and 60/720,596 filed Sep. 26, 2005; the entire disclosures of which are incorporated herein by reference.

TECHNICAL FIELD OF THE INVENTION

The present invention relates to compounds useful as inhibitors of kinases. The invention also relates to pharmaceutically acceptable compositions comprising the compounds of the invention, methods of using the compounds and compositions in the treatment of various disorders, and processes for preparing the compounds.

BACKGROUND OF THE INVENTION

The search for new therapeutic agents has been greatly aided in recent years by a better understanding of the structure of enzymes and other biomolecules associated with target diseases. One important class of enzymes that has been the subject of extensive study is protein kinases.

Protein kinases constitute a large family of structurally related enzymes that are responsible for the control of a variety of signal transduction processes within the cell. Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families.

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function.

These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and H2O2), cytokines (e.g., interleukin-1 (IL-1) and tumor necrosis factor a (TNF-a)), and growth factors (e.g., granulocyte macrophage-colony-stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Accordingly, there has been a substantial effort in medicinal chemistry to find protein kinase inhibitors that are effective as therapeutic agents. However, considering the lack of currently available treatment options for the majority of the conditions associated with protein kineses, there is still a great need for new therapeutic agents that inhibit these protein targets.

The Aurora proteins are a family of three highly related serine/threonine kinases (termed Aurora-A, -B and -C) that are essential for progression through the mitotic phase of cell cycle. Specifically Aurora-A plays a crucial role in centrosome maturation and segregation, formation of the mitotic spindle and faithful segregation of chromosomes. Aurora-B is a chromosomal passenger protein that plays a central role in regulating the alignment of chromosomes on the meta-phase plate, the spindle assembly checkpoint and for the correct completion of cytokinesis.

Overexpression of Aurora-A, -B or -C has been observed in a range of human cancers including colorectal, ovarian, gastric and invasive duct adenocarcinomas.

A number of studies have now demonstrated that depletion or inhibition of Aurora-A or -B in human cancer cell lines by siRNA, dominant negative or neutralizing antibodies disrupts progression through mitosis with accumulation of cells with 4N DNA, and in some cases this is followed by endoreduplication and cell death.

Protein kinases are attractive and proven targets for new therapeutic agents to treat a range of human diseases, with examples of kinase inhibitors including Gleevec® and Tarceva®. The Aurora kinases are especially attractive due to their association with numerous human cancers and the roles they play in the proliferation of these cancer cells. Therefore, there is a need for compounds that inhibit protein kinases.

SUMMARY OF THE INVENTION

This invention provides compounds and pharmaceutically acceptable compositions thereof that are useful as inhibitors of protein kinases, such as Aurora protein kinases (Aurora A, Aurora B, Aurora C) and FLT-3 kinase. These compounds are represented by formula I:

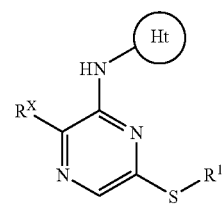

or a pharmaceutically acceptable salt thereof, wherein $R^1$, $R^X$ and the Ht ring are as defined herein.

These compounds and pharmaceutically acceptable compositions thereof are useful for inhibiting kinases in vitro, in vivo, and ex vivo. Such uses include treating or preventing a variety of diseases, disorders or conditions, including, but not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases. Other uses include the study of kinases in biological and pathological phenomena; the study of intracellular signal transduction pathways mediated by such kinases; and the comparative evaluation of new kinase inhibitors.

DETAILED DESCRIPTION OF THE INVENTION

The present invention provides a compound of formula I:

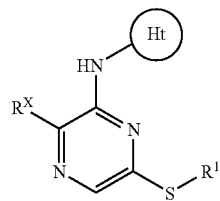

I or a pharmaceutically acceptable salt thereof, wherein:

Ht is a pyrazole ring or a thiazole ring, wherein each ring is optionally and independently substituted with $R^2$ and $R^{2'}$;

$R^x$ is T-$R^3$ or L-Z-$R^3$;

$R^1$ is a 5-7 membered monocyclic ring or 8-10 membered bicyclic ring selected from aryl, heteroaryl, heterocyclyl or carbocyclyl, said heteroaryl or heterocyclyl ring having 1-4 ring heteroatoms selected from nitrogen, oxygen or sulfur, wherein each substitutable ring carbon of Ring D is independently substituted by oxo, T-$R^5$, or V—Z—$R^5$, and each substitutable ring nitrogen of Ring D is independently substituted by —$R^4$;

T is a valence bond or a $C_{1-4}$ alkylidene chain;

Z is a $C_{1-4}$ alkylidene chain;

L is —O—, —S—, —SO—, —SO$_2$—, —N($R^6$)SO$_2$—, —SO$_2$N($R^6$)—, —N($R^6$)—, —CO—, —CO$_2$—, —N($R^6$)CO—, —N($R^6$)C(O)O—, —N($R^6$)CON($R^6$)—, —N($R^6$)SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON($R^6$)—;

$R^2$ and $R^{2'}$ are independently —R, -T-W—$R^6$, or $R^8$, or $R^2$ and $R^{2'}$ are taken together with their intervening atoms to form a fused, 5-8 membered, unsaturated or partially unsaturated, ring having 0-3 ring heteroatoms selected from nitrogen, oxygen, or sulfur, wherein each substitutable ring carbon of said fused ring formed by $R^2$ and $R^{2'}$ is independently substituted by halo, oxo, —CN, —NO$_2$, —$R^7$, or —V—$R^6$, and each substitutable ring nitrogen of said ring formed by $R^2$ and $R^{2'}$ is independently substituted by $R^4$;

each $R^3$ and $R^5$ is independently —R, -halo, —OR, —C(=O)R, —CO$_2$R, —COCOR, COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=O)R, —N($R^7$)COR, —N($R^7$) CO$_2$ ($C_{1-6}$ aliphatic), —N($R^4$)N($R^4$)$_2$, —C=NN($R^4$)$_2$, —C=N—OR, —N($R^7$)CON($R^7$)$_2$, —N($R^7$)SO$_2$N($R^7$)$_2$, —N($R^4$)SO$_2$R, or —OC(=O)N($R^7$)$_2$;

each R is hydrogen, a $C_{1-6}$ aliphatic group, a $C_{6-10}$ aryl ring, a heteroaryl ring having 5-10 ring atoms, or a heterocyclyl ring having 5-10 ring atoms, the heteroaryl or heterocyclyl ring having 1-4 ring heteroatoms selected from nitrogen, oxygen, or sulfur, the aliphatic group and each R ring being optionally substituted by $R^9$;

each $R^4$ is —$R^7$, —COR$^7$, —CO$_2$(optionally substituted $C_{1-6}$ aliphatic), —CON($R^7$)$_2$, or —SO$_2$R$^7$;

V is —O—, —S—, —SO—, —SO$_2$—, —N($R^6$)SO$_2$—, —SO$_2$N($R^6$)—, —N($R^6$)—, —CO—, —CO$_2$—, —N($R^6$) CO—, —N($R^6$)C(O)O—, —N($R^6$)CON($R^6$)—, —N($R^6$) SO$_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)SO$_2$N($R^6$)—, or —C($R^6$)$_2$N($R^6$)CON($R^6$)—;

W is —C($R^6$)$_2$O—, —C($R^6$)$_2$S—, —C($R^6$)$_2$SO—, —C($R^6$)$_2$SO$_2$—, —C($R^6$)$_2$SO$_2$N($R^6$)—, —C($R^6$)$_2$N($R^6$)—, —CO—, —CO$_2$—, —C($R^6$)OC(O)—, —C($R^6$)OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$) N($R^6$)—, —C($R^6$)$_2$N($R^6$)SO$_2$N($R^6$)—, —C($R^6$)$_2$N($R^6$)CON($R^6$)—, or —CON($R^6$)—;

each $R^6$ is independently hydrogen or an optionally substituted $C_{1-6}$ aliphatic group, or two $R^6$ groups on the same nitrogen atom are taken together with the nitrogen atom to form a 5-6 membered heterocyclyl or heteroaryl ring; and each $R^7$ is independently hydrogen or an optionally substituted $C_{1-6}$ aliphatic group, or two $R^7$ on the same nitrogen are taken together with the nitrogen to form a 5-8 membered heterocyclyl or heteroaryl ring;

each $R^8$ is halogen, —CN, or —NO$_2$;

each $R^9$ is —R', -halo, —OR', —C(=O)R', —CO$_2$R', —COCOR', COCH$_2$COR', —NO$_2$, —CN, —S(O)R', —S(O)$_2$R', —SR', —N(R')$_2$, —CON(R')$_2$, —SO$_2$N(R')$_2$, —OC(=O)R', —N(R')COR', —N(R')CO$_2$($C_{1-6}$ aliphatic), —N(R') N(R')$_2$, —C=NN(R')$_2$, —C=N—OR', —N(R') CON(R')$_2$, —N(R')SO$_2$N(R')$_2$, —N(R')SO$_2$R', or —OC(=O)N(R')$_2$; and each R' is independently hydrogen or a $C_{1-6}$ aliphatic group (which is unsubstituted in certain embodiments).

In some embodiments, the present invention provides a compound of formula I:

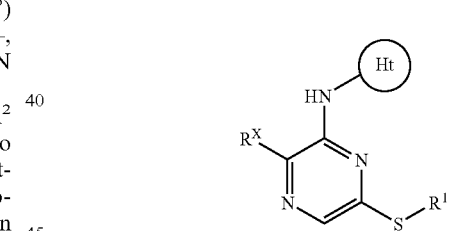

I or a pharmaceutically acceptable salt thereof, wherein

Ht is pyrazole or thiazole, wherein each ring is optionally and independently substituted with $R^2$ and $R^{2'}$;

$R^x$ is H, $C_{1-6}$aliphatic, NO$_2$, CN, halo, NH$_2$, N($C_{1-4}$aliphatic), N($C_{1-4}$aliphatic)$_2$, O($C_{1-4}$aliphatic), OH, or —N(C=O) ($C_{1-4}$aliphatic); wherein said aliphatic is optionally substituted with 1-3 fluoro;

$R^1$ is a 5-7 membered monocyclic ring or 8-10 membered bicyclic ring selected from aryl, heteroaryl, heterocyclyl or carbocyclyl, said heteroaryl or heterocyclyl ring having 1-4 ring heteroatoms selected from nitrogen, oxygen or sulfur, wherein each substitutable ring carbon is independently substituted by oxo, T-$R^5$, or V—Z—$R^5$, and each substitutable ring nitrogen is independently substituted by —$R^4$;

T is a valence bond or a $C_{1-4}$ alkylidene chain;

Z is a valence bond or a $C_{1-4}$ alkylidene chain;

$R^2$ and $R^{2'}$ are independently —R, -T-W—$R^6$, or $R^8$; or $R^2$ and $R^{2'}$ are taken together with their intervening atoms to form a fused, 5-8 membered, unsaturated or partially unsaturated, ring having 0-3 ring heteroatoms selected from nitrogen, oxygen, or sulfur, wherein each substitutable ring carbon of said fused ring formed by $R^2$ and $R^{2'}$ is independently substituted by halo, oxo, —CN, —$NO_2$, —$R^7$, or —V—$R^6$, and each substitutable ring nitrogen of said ring formed by $R^2$ and $R^{2'}$ is independently substituted by $R^4$;

each $R^5$ is independently —R, -halo, —OR, —C(=O)R, —$CO_2$R, —COCOR, $COCH_2COR$, —$NO_2$, —CN, —S(O) R, —$S(O)_2$R, —SR, —$N(R^4)_2$, —$CON(R^7)_2$, —$SO_2N(R^7)_2$, —OC(=O)R, —$N(R^7)$COR, —$N(R^7)CO_2(C_{1-6}$ aliphatic), —$N(R^4)N(R^4)_2$, —C=$NN(R^4)_2$, —C=N—OR, —$N(R^7)$ $CON(R^7)_2$, —$N(R^7)SO_2N(R^7)_2$, —$N(R^4)SO_2R$, or —OC(=O)$N(R^7)_2$;

each R is hydrogen, a $C_{1-6}$aliphatic group, a $C_{6-10}$ aryl ring, a heteroaryl ring having 5-10 ring atoms, or a heterocyclyl ring having 4-10 ring atoms, the heteroaryl or heterocyclyl ring having 1-4 ring heteroatoms selected from nitrogen, oxygen, or sulfur, the aliphatic group and each R ring being optionally substituted by $R^9$;

each $R^4$ is —$R^7$, —$COR^7$, —$CO_2$(optionally substituted $C_{1-6}$ aliphatic), —$CON(R^7)_2$, or —$SO_2R^7$;

V is —O—, —S—, —SO—, —$SO_2$—, —$N(R^6)SO_2$—, —$SO_2N(R^6)$—, —$N(R^6)$—, —CO—, —$CO_2$—, —$N(R^6)$ CO—, —$N(R^6)C(O)O$—, —$N(R^6)CON(R^6)$—, —$N(R^6)$ $SO_2N(R^6)$—, —$N(R^6)N(R^6)$—, —C(O)$N(R^6)$—, —OC(O) $N(R^6)$—, —$C(R^6)_2O$—, —$C(R^6)_2S$—, —$C(R^6)_2SO$—, —$C(R^6)_2SO_2$—, —$C(R^6)_2SO_2N(R^6)$—, $C(R^6)_2N(R^6)$—, —$C(R^6)_2N(R^6)C(O)$—, —$C(R^6)_2N(R^6)C(O)O$—, $C(R^6)$ =$NN(R^6)$—, —$C(R^6)$=N—O—, —$C(R^6)_2N(R^6)N(R^6)$—, —$C(R^6)_2N(R^6)SO_2N(R^6)$—, or —$C(R^6)_2N(R^6)CON(R^6)$—;

W is —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —CO—, —$CO_2$—, —$C(R^6)_2OC(O)$—, —$C(R^6)_2OC(O)N(R^6)$—, —$C(R^6)_2N(R^6)CO$—, —$C(R^6)_2N(R^6)C(O)O$—, —$C(R^6)$=$NN(R^6)$—, —$C(R^6)$=N—O—, —$C(R^6)_2N(R^6)$ $N(R^6)$—, —$C(R^6)_2N(R^6)SO_2N(R^6)$—, —$C(R^6)_2N(R^6)CON(R^6)$—, or —$CON(R^6)$—;

each $R^6$ is independently hydrogen or $C_{1-6}$ aliphatic optionally substituted with 1-3 halogen; or two $R^6$ groups on the same nitrogen atom are taken together with the nitrogen atom to form a 4-6 membered heterocyclyl or 5-6 membered heteroaryl ring; and each $R^7$ is independently hydrogen or $C_{1-6}$ aliphatic optionally substituted with 1-3 halogen; or two $R^7$ on the same nitrogen are taken together with the nitrogen to form a 4-8 membered heterocyclyl or 5-8 heteroaryl ring;

each $R^8$ is halogen, —CN, or —$NO_2$;

each $R^9$ is —R', -halo, —OR', —C(=O)R', —$CO_2$R', —COCOR', $COCH_2COR$', —$NO_2$, —CN, —S(O)R', —$S(O)_2R'$, —SR', —$N(R')_2$, —$CON(R')_2$, —$SO_2N(R')_2$, —OC(=O)R', —$N(R')$COR', —$N(R')CO_2(C_{1-6}$ aliphatic), —$N(R')N(R')_2$, —C=$NN(R')_2$, —C=N—OR', —$N(R')$ $CON(R')_2$, —$N(R')SO_2N(R')_2$, —$N(R')SO_2R'$, —OC(=O)N $(R')_2$, =$NN(R')_2$, =N—OR', or =O and each R' is independently hydrogen or a $C_{1-6}$ aliphatic group optionally substituted with 0-4 occurrences of $NH_2$, $NH(C_{1-4}$aliphatic), $N(C_{1-4}$aliphatic$)_2$, halogen, $C_{1-4}$aliphatic, OH, $O(C_{1-4}$aliphatic), $NO_2$, CN, $CO_2H$, $CO_2(C_{1-4}$aliphatic), $O(haloC_{1-4}$ aliphatic), or $haloC_{1-4}$aliphatic; or, two R' together with the atom(s) to which they are attached, form an optionally substituted 3-6 membered carbocyclyl or heterocyclyl.

In one embodiment, Ht is

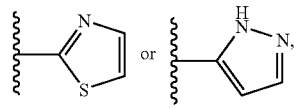

wherein each ring is optionally and independently substituted with $R^2$ and $R^{2'}$.

In certain embodiments, the substituents in $R^6$ and $R^7$ are independently selected from $R^9$.

In another embodiment, the optionally substituted aliphatic group of $R^6$ is a $C_{1-4}$ aliphatic group. In some embodiments, the aliphatic group is optionally substituted with 1-3 halogen.

In another embodiment $R^2$ is H or $C_{1-6}$ aliphatic (which is unsubstituted in certain embodiments).

In another embodiment $R^2$ is H or $C_{1-3}$ aliphatic (which is unsubstituted in certain embodiments).

In another embodiment $R^2$ is H or $C_{1-3}$ aliphatic (which is unsubstituted in certain embodiments).

In one embodiment, $R^x$ is —R, halogen, $NO_2$, CN, $CO_2R$, OR, or —SR. In another embodiment, $R^x$ is H or F. In yet another embodiment, $R^x$ is H.

In another embodiment, $R^x$ is H, $C_{1-6}$aliphatic, $NO_2$, CN, halo, $NH_2$, $N(C_{1-4}$aliphatic), $N(C_{1-4}$aliphatic$)_2$, $O(C_{1-4}$aliphatic), OH, or $N(C=O)(C_{1-4}$aliphatic). In some embodiment, $R^x$ is H, $C_{1-6}$aliphatic, $NO_2$, CN, halo, $NH_2$, $N(C_{1-4}$aliphatic), or —$N(C=O)(C_{1-4}$aliphatic). In some embodiments, said aliphatic is optionally substituted with 1-3 fluoro.

In one embodiment, $R^1$ is an optionally substituted 5-6 membered monocyclic aryl or heteroaryl. In another embodiment, $R^1$ is an optionally substituted phenyl. In some embodiments, $R^1$ is substituted in the 4-position with $T^4-R^5$.

In one embodiment, $R^5$ is —$N(R^7)$COR or —$CON(R^7)_2$.

In another embodiment, T is a valence bond.

In one embodiment, a compound of this invention is represented by formula Ia:

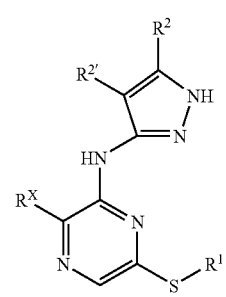

Ia wherein the variables are as defined in any embodiment herein.

In one embodiment, a compound of this invention is represented by formula Ib:

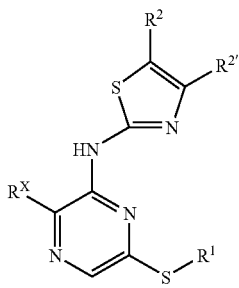

wherein the variables are as defined in any embodiment herein.

In a preferred form of formula Ib, $R^{2'}$ is hydrogen.

In one embodiment, this invention includes compounds I-1 and I-2 (or a pharmaceutically acceptable salt thereof):

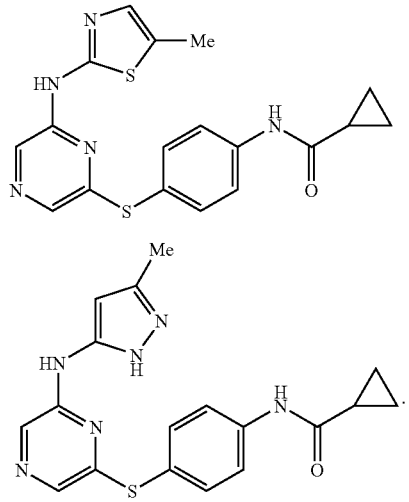

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", and the like, as used herein, means an unbranched or branched, straight-chain or cyclic, substituted or unsubstituted hydrocarbon that is completely saturated or that contains one or more units of unsaturation that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl" or "cycloalkyl" and the like) refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopropenyl, and cyclobutyl.

In the compounds of this invention, rings include linearly-fused, bridged, or spirocyclic rings. Examples of bridged cycloaliphatic groups include, but are not limited to, bicyclo [3.3.2]decane, bicyclo[3.1.1]heptane, and bicyclo[3.2.2] nonane.

The term "heterocycle", "heterocyclyl", "heterocycloaliphatic", or "heterocyclic", and the like, as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members. Examples of bridged heterocycles include, but are not limited to, 7-aza-bicyclo[2.2.1]heptane and 3-aza-bicyclo[3.2.2] nonane.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —R$^o$; —OR$^o$; —SR$^o$; phenyl (Ph) optionally substituted with R$^o$; —O(Ph) optionally substituted with R$^o$; —(CH$_2$)$_{1-2}$(Ph), optionally substituted with R$^o$; —CH=CH(Ph), optionally substituted with R$^o$; a 5-6 membered heteroaryl or heterocyclic ring optionally substituted with R$^o$; —NO$_2$; —CN; —N(R$^o$)$_2$; —NR$^o$C(O)R$^o$; —NR$^o$C(S)R$^o$; —NR$^o$C(O)N(R$^o$)$_2$; —NR$^o$C(S)N(R$^o$)$_2$; —NR$^o$CO$_2$R$^o$; —NR$^o$NR$^o$C(O)R$^o$; —NR$^o$NR$^o$C(O)N(R$^o$)$_2$; —NR$^o$NR$^o$CO$_2$R$^o$; —C(O)C(O)R$^o$; —C(O)CH$_2$C(O)R$^o$; —CO$_2$R$^o$; —C(O)R$^o$; —C(S)R$^o$; —C(O)N(R$^o$)$_2$; —C(S)N(R$^o$)$_2$; —OC(O)N(R$^o$)$_2$; —OC(O)R$^o$; —C(O)N(OR$^o$)R$^o$; —C(NOR$^o$)R$^o$; —S(O)$_2$R$^o$; —S(O)$_3$R$^o$; —SO$_2$N(R$^o$)$_2$; —S(O)R$^o$; —NR$^o$SO$_2$N(R$^o$)$_2$; —NR$^o$SO$_2$R$^o$; —N(OR$^o$)R$^o$; —C(N=NH)—N(R$^o$)$_2$; —P(O)$_2$R$^o$; —PO(R$^o$)$_2$; —OPO(R$^o$)$_2$; or —(CH$_2$)$_{0-2}$NHC(O)R$^o$; wherein each independent occurrence of R$^o$ is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R$^o$, on the same substituent or different substituents, taken together with the atom(s) to which each R$^o$ group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of R$^o$ are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$aliphatic, wherein each of the foregoing C$_{1-4}$aliphatic groups of R$^o$ is unsubstituted.

An aliphatic group or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHSO$_2$(alkyl), or =NR*, where each R* is independently selected from hydrogen or an optionally substituted C$_{1-6}$ aliphatic group.

Unless otherwise defined above and herein, optional substituents on the nitrogen of a non-aromatic heterocyclic ring are generally selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^{+1}$)$_2$, —C(=NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of R$^+$ are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —CO$_2$H, —CO$_2$(C$_{1-4}$ aliphatic), —O(halo C$_{1-4}$ aliphatic), or halo(C$_{1-4}$ aliphatic), wherein each of the foregoing C$_{1-4}$aliphatic groups of R$^+$ is unsubstituted.

The term "alkylidene chain" refers to a straight or branched carbon chain that may be fully saturated or have one or more units of unsaturation and has two points of attachment to the rest of the molecule.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, and other editions of this book, the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, two independent occurrences of a group are taken together with the atom(s) to which they are bound to form a ring. This ring is an optionally substituted 3-12 membered saturated, partially unsaturated, or fully unsaturated monocyclic or bicyclic ring having 0-4 heteroatoms independently selected from nitrogen, oxygen, or sulfur.

Examples of such rings include, but are not limited to the following: piperidin-1-yl, piperazin-1-yl, or morpholin-4-yl group.

In some embodiments, an alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —CO$_2$—, —OC(O)—, —C(O)CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—, wherein R is defined herein. Unless otherwise specified, the optional replacements form a chemically stable compound. Optional interruptions can occur both within the chain and at either end of the chain; i.e., both at the point of attachment and/or also at the terminal end. Two optional replacements can also be adjacent to each other within a chain so long as it results in a chemically stable compound. Unless otherwise specified, if the replacement or interruption occurs at the terminal end, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention.

Unless otherwise stated, a substituent can freely rotate around any rotatable bonds. For example, a substituent drawn as

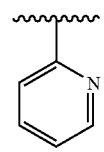

also represents

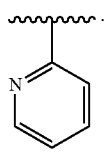

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The compounds of this invention may be prepared in general by methods known to those skilled in the art (see, e.g., WO 02/057259, which is incorporated herein by reference). Those compounds may be analyzed by known methods, including but not limited to LCMS (liquid chromatography mass spectrometry) and NMR (nuclear magnetic resonance).

Scheme 1 depicts a general synthesis that may be followed to prepare compounds of this invention. In this synthesis, a dichloro-piperazine compound 1 (substituted appropriately with R$^X$) is reacted with a thiol (HS—R$^1$) to provide compound 2. Appropriate thiols, as well as methods for making such thiols, are known in the art. Compound 2 is then reacted with an appropriate heterocyclic amine to provide a compound of formula I. Appropriate heterocyclic amines, i.e., pyrazole and thiazole amines, as well as methods for making such amines, are known in the art. Reagents for carrying out these reactions are known in the art (see, e.g., Sorrell & Smith, M. B. and March, J., supra). As would be recognized by skilled practitioners, protecting groups may be used in connection with the Scheme 1 synthesis (see, e.g., Greene, T. W., Wuts, P. G., supra).

Scheme 1.

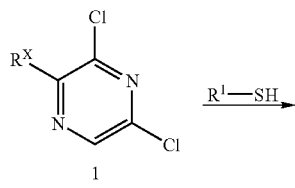

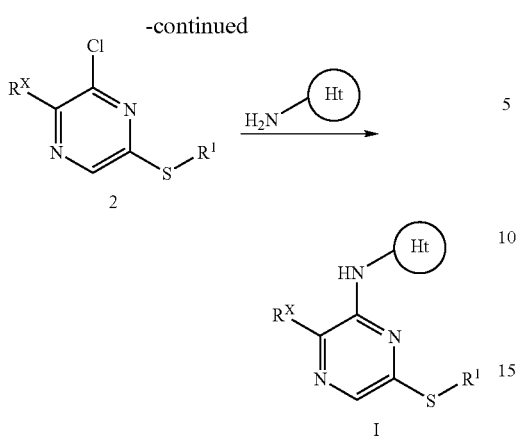

Accordingly, another embodiment of this invention provides a process for preparing a compound of formula I comprising reacting a compound 2 with a heterocyclic amine to provide a compound of formula I.

Another embodiment of this invention provides a process for preparing a compound of formula I comprising reacting a compound 1 with a thiol (HS—$R^1$) to provide a compound 2. In certain embodiments, this process further comprises reacting a compound 2 (prepared as described here) in the presence of a heterocyclic amine to provide a compound of formula I.

One embodiment provides a process of preparing a compound of formula I:

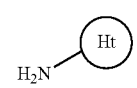

comprising reacting a compound of formula a:

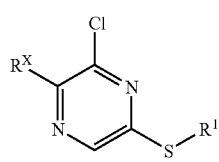

wherein Ht is as defined herein with a compound of formula 2:

2 wherein $R^X$ and $R^1$ are as defined herein, under suitable coupling conditions to form a compound of formula I. Suitable coupling conditions are known to one of skill in the art, and typically involve a palladium catalyst, a suitable solvent, and a base. Examples of catalysts include, but are not limited to, $PdCl_2(PPh_3)_2$, $Pd(Ph_3)_4$, $PdCl_2(dppf)$, and $Pd_2(dba)_3$. Examples of bases include, but are not limited to, $K_2CO_3$ and $Na_2CO_3$. Suitable solvents include, but are not limited to, dioxane, tetrahydrofuran, toluene, and ethanol.

One embodiment further comprises the step of reacting $R^1$—SH, wherein $R^1$ is as defined herein; with a compound of formula 1:

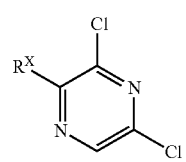

1 under suitable displacement conditions to form the compound of formula 2. Suitable displacement conditions are known to one of skill in the art and typically involve a non-nucleophilic base and a suitable solvent. Examples of non-nucleophilic bases include, but are not limited to, NaH, LDA, KH, and KotBu. Examples of suitable solvents include, but are not limited to, THF, DCM, acetonitrile, and DMF.

One aspect of this invention relates to a method for treating a disease state in patients that is alleviated by treatment with a protein kinase inhibitor, which method comprises administering to a patient in need of such a treatment a therapeutically effective amount of a compound of formula I (herein including Ia and Ib). The method is particularly useful for treating a disease state that is alleviated by the use of an inhibitor of a kinase, such as the Aurora kinases (Aurora A, Aurora B, Aurora C) or FLT-3.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Another aspect of this invention is directed towards a method of treating cancer in a subject in need thereof, comprising the sequential or co-administration of a compound of this invention or a pharmaceutically acceptable salt thereof, and an anti-cancer agent. In some embodiments, said anti-cancer agent is selected from camptothecin, doxorubicin, idarubicin, Cisplatin, taxol, taxotere, vincristine, tarceva, the MEK inhibitor, U0126, a KSP inhibitor, or vorinostat.

The protein kinase inhibitors or pharmaceutical salts thereof may be formulated into pharmaceutical compositions for administration to animals or humans. These pharmaceutical compositions, which comprise an amount of the protein inhibitor effective to treat or prevent kinase mediated condition and a pharmaceutically acceptable carrier, are another embodiment of the present invention.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}\text{ alkyl})_4$ salts. This invention also envisions the quaternization of any basic nitrogen-containing groups of the compounds disclosed herein. Water or oil-soluble or dispersible products may be obtained by such quaternization.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing a kinase-mediated condition comprising the step of administering to a patient one of the above-described pharmaceutical compositions. The term "patient", as used herein, means an animal, preferably a human.

The term "kinase-mediated condition," as used herein means diseases or other deleterious conditions in which a protein kinase is known to play a role. Such conditions include, without limitation, autoimmune diseases, inflammatory diseases, neurological and neurodegenerative diseases, cancer, cardiovascular diseases, allergy and asthma. In some embodiments, the term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions. In some embodiments, the cancer is selected from colorectal, thyroid, or breast cancer.

In some embodiments, the term "cancer" includes, but is not limited to the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon, adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; and leukemia.

Preferably, these methods are used to treat or prevent a condition selected from cancers such as cancers of the breast, colon, prostate, skin, pancreas, brain, genitourinary tract, lymphatic system, stomach, larynx and lung, including lung adenocarcinoma and small cell lung cancer; stroke, diabetes, myeloma, hepatomegaly, cardiomegaly, Alzheimer's disease, cystic fibrosis, and viral disease, or any specific disease or disorder described above.

In some embodiments, these methods are used to treat or prevent a condition selected from melanoma, myeloma, leukemia, lymphoma, neuroblastoma, or a cancer selected from colon, breast, gastric, ovarian, cervical, lung, central nervous system (CNS), renal, prostate, bladder, pancreatic, brain (gliomas), head and neck, kidney, liver, melanoma, sarcoma, or thyroid cancer.

According to another embodiment, the invention provides methods for treating or preventing a kinase-mediated condition comprising the step of administering to a patient a compound of formula I or a composition comprising said compound. In some embodiments, said kinase is an Aurora or FLT-3 kinase.

Another aspect of the invention relates to inhibiting kinase activity in a patient, which method comprises administering to the patient a compound of formula I or a composition comprising said compound. In some embodiments, said kinase is an Aurora or FLT-3 kinase. Another aspect of the invention relates to a method of treating cancer in a patient in need thereof comprising the step of disrupting mitosis of the cancer cells by inhibiting Aurora with a compound of this invention.

Another aspect of the invention relates to inhibiting kinase activity in a biological sample, which method comprises contacting said biological sample with a compound of formula I or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of kinase activity in a biological sample is useful for a variety of purposes that are known to one of skill in the art. Examples of such purposes include, but are not limited to, blood transfusion, organ-transplantation, biological specimen storage, and biological assays.

Depending upon the particular conditions to be treated or prevented, additional drugs, which are normally administered to treat or prevent that condition, may be administered together with the compounds of this invention. For example, chemotherapeutic agents or other anti-proliferative agents may be combined with the compounds of this invention to treat proliferative diseases. In some embodiments, to treat cancer.

Those additional agents may be administered separately, as part of a multiple dosage regimen, from the kinase inhibitor-containing compound or composition. Alternatively, those agents may be part of a single dosage form, mixed together with the kinase inhibitor in a single composition.

Methods for evaluating the activity of the compounds of this invention (e.g., kinase assays) are known in the art and also shown in the examples below. In order that this invention be more fully understood, the following preparative and testing examples are set forth. These examples are for the purpose of illustration only and are not to be construed as limiting the scope of the invention in any way.

Compounds I-1 and I-2 were prepared and analysed as follows.

EXAMPLE 1

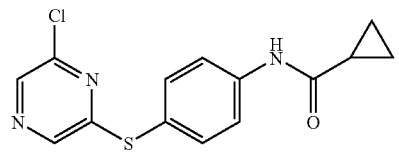

N-(4-(6-chloropyrazin-2-ylthio)phenyl)cyclopropan-
ecarboxamide

To a solution of N-(4-mercaptophenyl)cyclopropane carboxamide (16.1 mmol) in THF (25 mL) at 0° C. was added sodium hydride (16.1 mmol) portionwise. Once the addition was complete the resulting solution was stirred at room temperature for 30 min. After this time, the reaction mixture was cooled to 0° C. and a solution of 2,6-dichloropyrazine (13.4 mmol) was added and the resulting mixture stirred at room temperature for 16 h. Water (30 mL) and ethyl acetate (30 mL) were added and the layers separated. The aqueous layer was extracted further with ethyl acetate (2×30 mL), the combined organic layers dried (MgSO$_4$) and concentrated in vacuo. The residue was purified by column chromatography (EtOAc/Petroleum ether, 0-100% gradient EtOAc) to give the title compound (2.95 g, 72%) as a cream coloured solid; $^1$H NMR (400 MHz, DMSO-d6) δ 0.91 (2H, m), 1.13 (2H, m), 1.54 (1H, m), 7.53 (1H, br s), 7.57 (2H, m), 7.65 (2H, m), 7.96 (1H, s), 8.22 (1H, s); MS (ES+): m/e=306.14 (100%).

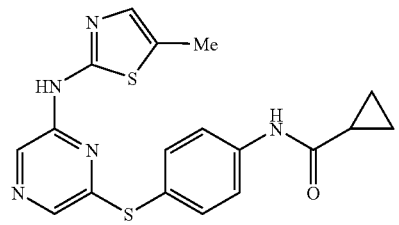

N-(4-(6-(5-methylthiazol-2ylamino)pyrazin-2-ylthio)
phenyl)cyclopropanecarboxamide (I-1)

To a solution of N-(4-(6-chloropyrazin-2-ylthio)phenyl)cyclopropanecarboxamide (0.82 mmol) and 2-amino-5-methylthiazole (0.86 mmol) in 1,4-dioxan (3 mL), 4,5-bis(diphenylphosphino)-9,9-dimethylxanthene (0.05 mmol), tris(dibenzylideneacetone)dipalladium (0.03 mmol) and sodium carbonate (1.15 mmol) were added. The resulting solution was heated at 120° C. in the microwave (175 W, 25 psi) for 3 h. Water (10 mL) and ethyl acetate (10 mL) were added and the layers separated. The aqueous layer was extracted further with ethyl acetate (2×10 mL), the combined organic layers dried (MgSO$_4$) and concentrated in vacuo. The residue was purified by column chromatography eluting with MeOH:CH$_2$Cl$_2$ (1:20) to give the title compound (42.5 mg, 14%) as a light brown solid; $^1$H NMR (400 MHz, DMSO-d6) δ 0.81 (4H, m), 1.82 (1H, m), 2.16 (3H, s), 3.32 masked signal, 6.99 (1H, m), 7.58 (2H, m), 7.76 (2H, m), 7.84 (1H, s), 8.04 (1H, s), 10.49 (1H, s), 11.50 (1H, br s); MS (ES+): m/e=384.48 (100%).

EXAMPLE 2

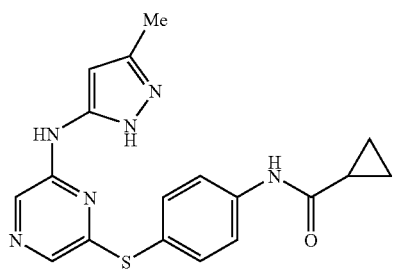

N-(4-(6-(3-methyl-1H-pyrazol-5-ylamino)pyrazin-2-ylthio)phenyl)cyclopropanecarboxamide (I-2)

To a solution of N-(4-(6-chloropyrazin-2-ylthio)phenyl) cyclopropanecarboxamide (0.49 mmol) and 3-amino-5-methylpyrazole (0.52 mmol) in 1,4-dioxan (3 mL), 4,5-bis (diphenylphosphino)-9,9-dimethylxanthene (0.03 mmol), tris(dibenzylideneacetone) dipalladium (0.02 mmol) and sodium carbonate (0.69 mmol) were added. The resulting solution was heated at 120° C. in the microwave (175 W, 25 psi) for 30 min. Water (10 mL) and ethyl acetate (10 mL) were added and the layers separated. The aqueous layer was extracted further with ethyl acetate (2×10 mL), the combined organic layers dried (MgSO$_4$) and concentrated in vacuo. The residue was purified by column chromatography (EtOAc/ Petroleum ether, 0-100% gradient EtOAc) and then purified further using mass directed HPLC purification (sunfire C18 column, trifluoroacetic acid/MeCN/MeOH as eluent) to give the title compound (10.6 mg, 6%) as a light yellow solid; $^1$H NMR (400 MHz, DMSO-d6) δ 0.81 (4H, m), 1.83 (1H, m), 2.05 (3H, s), 5.55 (1H, s), 7.54 (2H, m), 7.59 (1H, s), 7.74 (2H, m), 8.02 (1H, s), 9.77 (1H, s), 10.47 (1H, s); MS (ES+): m/e=367.41 (100%).

EXAMPLE 3

Aurora-2 (Aurora A) Inhibition Assay

Compounds are screened for their ability to inhibit Aurora-2 using a standard coupled enzyme assay (Fox et al., Protein Sci., (1998) 7, 2249). Assays are carried out in a mixture of 100 mM Hepes (pH7.5), 100 mM MgCl$_2$, 1 mM DTT, 25 mM NaCl, 2.5 mM phosphoenolpyruvate, 300 µM NADH, 30 µg/ml pyruvate kinase and 10 µg/ml lactate dehydrogenase. Final substrate concentrations in the assay are 400 µM ATP (Sigma Chemicals) and 570 µM peptide (Kemptide, American Peptide, Sunnyvale, Calif.). Assays are carried out at 30° C. and in the presence of 40 nM Aurora-2.

An assay stock buffer solution is prepared containing all of the reagents listed above, with the exception of Aurora-2 and the test compound of interest. 55 µl of the stock solution is placed in a 96 well plate followed by addition of 2 µl of DMSO stock containing serial dilutions of the test compound (typically starting from a final concentration of 7.5 µM). The plate is preincubated for 10 minutes at 30° C. and the reaction initiated by addition of 10 µl of Aurora-2. Initial reaction rates are determined with a Molecular Devices SpectraMax Plus plate reader over a 10 minute time course. IC50 and Ki data are calculated from non-linear regression analysis using the Prism software package (GraphPad Prism version 3.0cx for Macintosh, GraphPad Software, San Diego Calif., USA). Compounds I-1 and I-2 inhibit Aurora-2 at a Ki value of <0.1 uM.

EXAMPLE 4

Aurora-1 (Aurora B) Inhibition Assay (Radiometric)

An assay buffer solution is prepared which consisted of 25 mM HEPES (pH 7.5), 10 mM MgCl$_2$, 0.1% BSA and 10% glycerol. A 22 nM Aurora-B solution, also containing 1.7 mM DTT and 1.5 mM Kemptide (LRRASLG), is prepared in assay buffer. To 22 µL of the Aurora-B solution, in a 96-well plate, is added 2 µl of a compound stock solution in DMSO and the mixture allowed to equilibrate for 10 minutes at 25° C. The enzyme reaction is initiated by the addition of 16 µl stock [γ-$^{33}$P]-ATP solution (~20 nCi/µL) prepared in assay buffer, to a final assay concentration of 800 µM. The reaction is stopped after 3 hours by the addition of 16 µL 500 mM phosphoric acid and the levels of $^{33}$P incorporation into the peptide substrate are determined by the following method. A phosphocellulose 96-well plate (Millipore, Cat no. MAPH-NOB50) is pre-treated with 100 µL of a 100 mM phosphoric acid prior to the addition of the enzyme reaction mixture (40 µL). The solution is left to soak on to the phosphocellulose membrane for 30 minutes and the plate subsequently washed four times with 200 µL of a 100 mM phosphoric acid. To each well of the dry plate is added 30 µL of Optiphase 'SuperMix' liquid scintillation cocktail (Perkin Elmer) prior to scintillation counting (1450 Microbeta Liquid Scintillation Counter, Wallac). Levels of non-enzyme catalysed background radioactivity are determined by adding 16 µL of the 500 mM phosphoric acid to control wells, containing all assay components (which acts to denature the enzyme), prior to the addition of the [γ-$^{33}$P]-ATP solution. Levels of enzyme catalysed $^{33}$P incorporation are calculated by subtracting mean background counts from those measured at each inhibitor concentration. For each Ki determination 8 data points, typically covering the concentration range 0-10 µM compound, are obtained in duplicate (DMSO stocks are prepared from an initial compound stock of 10 mM with subsequent 1:2.5 serial dilutions). Ki values are calculated from initial rate data by non-linear regression using the Prism software package (Prism 3.0, Graphpad Software, San Diego, Calif.). Compounds I-2 inhibit Aurora-2 at a Ki value of <1.0 uM.

EXAMPLE 5

FLT-3 Inhibition Assay

Compounds are screened for their ability to inhibit FLT-3 activity using a radiometric filter-binding assay. This assay monitors the 33P incorporation into a substrate poly(Glu, Tyr) 4:1 (pE4Y). Reactions are carried out in a solution containing 100 mM HEPES (pH 7.5), 10 mM MgCl$_2$, 25 mM NaCl, 1 mM DTT, 0.01% BSA and 2.5% DMSO. Final substrate concentrations in the assay are 90 µM ATP and 0.5 mg/ml pE4Y (both from Sigma Chemicals, St Louis, Mo.). The final concentration of a compound of the present invention is generally between 0.01 and 5 µM. Typically, a 12-point titration is conducted by preparing serial dilutions from 10 mM DMSO stock of test compound. Reactions are carried out at room temperature.

Two assay solutions are prepared. Solution 1 contains 100 mM HEPES (pH 7.5), 10 mM MgCl$_2$, 25 mM NaCl, 1 mg/ml pE4Y and 180 mM ATP (containing 0.3 mCi of [γ-33$^P$]ATP for each reaction). Solution 2 contains 100 mM HEPES (pH 7.5), 10 mM MgCl$_2$, 25 mM NaCl, 2 mM DTT, 0.02% BSA and 3 nM FLT-3. The assay is run on a 96 well plate by mixing 50 μl each of Solution 1 and 2.5 ml of the compounds of the present invention. The reaction is initiated with Solution 2. After incubation for 20 minutes at room temperature, the reaction is stopped with 50 μl of 20% TCA containing 0.4 mM of ATP. All of the reaction volume is then transferred to a filter plate and washed with 5% TCA by a Harvester 9600 from TOMTEC (Hamden, Conn.). The amount of $^{33}$P incorporation into pE4y is analyzed by a Packard Top Count Microplate Scintillation Counter (Meriden, Conn.). The data is fitted using Prism software to get an IC50 or Ki. Compounds I-1 and I-2 inhibit FLT-3 at a Ki value of <1.0 uM.

All documents cited herein are hereby incorporated by reference.

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:
1. A compound of formula I:

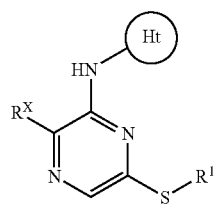

I or a pharmaceutically acceptable salt thereof, wherein
Ht is pyrazole or thiazole, wherein each ring is optionally and independently substituted with $C_{1-6}$ aliphatic and $R^8$;
$R^x$ is H, $C_{1-6}$aliphatic, $NO_2$, CN, halo, $NH_2$, $NH(C_{1-4}aliphatic)$, $N(C_{1-4}aliphatic)_2$, $O(C_{1-4}aliphatic)$, OH, or —N(C=O)($C_{1-4}aliphatic$); wherein said aliphatic is optionally substituted with 1-3 fluoro;
$R^1$ is aryl, wherein each substitutable ring carbon is independently substituted by $N(R^7)COR$, halo and $C_{1-6}$ aliphatic;
each R is hydrogen, a $C_{1-6}$ aliphatic group, a $C_{6-10}$ aryl ring, a heteroaryl ring having 5-10 ring atoms, or a heterocyclyl ring having 5-10 ring atoms, the heteroaryl or heterocyclyl ring having 1-4 ring heteroatoms selected from nitrogen, oxygen, or sulfur, the aliphatic group and each R ring being optionally substituted by $R^9$;
each $R^7$ is independently hydrogen or $C_{1-6}$ aliphatic optionally substituted with 1-3 halogen;
each $R^8$ is halogen, CN, or $NO_2$;
each $R^9$ is —R', -halo, —OR', —C(=O)R', —$CO_2$R', —COCOR', $COCH_2COR'$, —$NO_2$, —CN, —S(O)R', —$S(O)_2R'$, —SR', —$N(R')_2$, —$CON(R')_2$, —$SO_2N(R')_2$, —OC(=O)R', —N(R')COR', —N(R')$CO_2$($C_{1-6}$ aliphatic), —N(R')N(R')$_2$, —C=NN(R')$_2$, —C=N—OR', —N(R')CON(R')$_2$, —N(R')$SO_2$N(R')$_2$, —N(R')$SO_2$R', —OC(=O)N(R')$_2$, =NN(R)$_2$, =N—OR', or =O and
each R' is independently hydrogen or a $C_{1-6}$ aliphatic group optionally substituted with 0-4 occurrences of $NH_2$, $NH(C_{1-4}aliphatic)$, $N(C_{1-4}aliphatic)_2$, halogen, $C_{1-4}aliphatic$, OH, $O(C_{1-4}aliphatic)$, $NO_2$, CN, $CO_2H$, $CO_2(C_{1-4}aliphatic)$, $O(haloC_{1-4}$ aliphatic), or halo$C_{1-4}$aliphatic; or, two R', together with the atom(s) to which they are attached, form an optionally substituted 3-6 membered carbocyclyl or heterocyclyl.

2. The compound according to claim 1, wherein Ht is

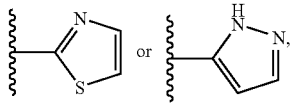

wherein each ring is optionally and independently substituted with $C_{1-6}$ aliphatic, halogen, —CN or —$NO_2$.

3. The compound according to claim 1 or claim 2, wherein each substitutable ring carbon of Ht is independently substitutable with $C_{1-6}$ alkyl.

4. The compound according to claim 1, wherein $R^x$ is H, $C_{1-6}$aliphatic, $NO_2$, CN, halo, $O(C_{1-4}aliphatic)$ or OH.

5. The compound according to claim 4, wherein $R^x$ is H or F.

6. The compound according to claim 5, wherein $R^x$ is H.

7. The compound according to claim 1, wherein $R^1$ is a 6 membered monocyclic aryl.

8. The compound according to claim 1 as represented by formula Ia:

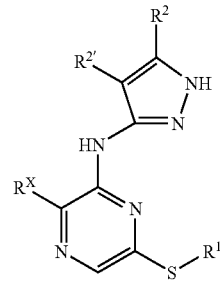

Ia wherein:
$R^2$ and $R^{2'}$ is H, $C_{1-6}$ aliphatic, halogen, —CN or —$NO_2$.

9. The compound according to claim 1, as represented by formula Ib:

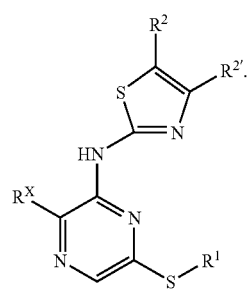

Ib wherein:
$R^2$ and $R^{2'}$ is H, $C_{1-6}$ aliphatic, halogen, —CN or —NO$_2$.
10. The compound according to claim 1, selected from the following:
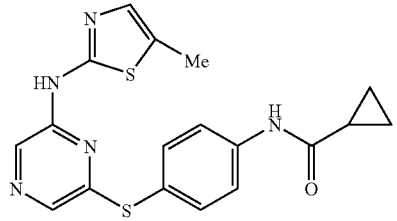
I-1
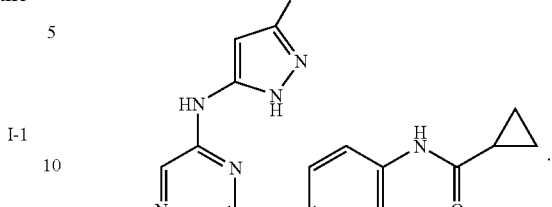
I-2
11. A pharmaceutical composition comprising a compound of claim 1 and a pharmaceutically acceptable carrier, adjuvant, or vehicle.
* * * * *